United States Patent [19]

Stanley, Jr. et al.

[11] Patent Number: 5,206,142
[45] Date of Patent: Apr. 27, 1993

[54] *ENTAMOEBA HISTOLYTICA* DIAGNOSTIC ASSAY

[75] Inventors: Samuel L. Stanley, Jr.; Ellen Li, both of St. Louis, Mo.

[73] Assignee: Washington University, St. Louis, Mo.

[21] Appl. No.: 874,312

[22] Filed: Apr. 27, 1992

Related U.S. Application Data

[62] Division of Ser. No. 516,388, Apr. 30, 1990, Pat. No. 5,130,417.

[51] Int. Cl.$^5$ .......................................... G01N 33/569
[52] U.S. Cl. ................................................... 435/7.22
[58] Field of Search ........................... 536/27; 435/7.22

[56] References Cited

U.S. PATENT DOCUMENTS 4,762,789 8/1988 Keene et al. .......................... 435/219

OTHER PUBLICATIONS

ATCC Catalog of Protists, 17th Edition, 1991 pp. 20–21.
Tannich et al., Proc. Natl. Acad. Sci. USA 86, 5118 (1989).
Hardy & Strauss, Chem. Absts. 108:128277 (1988).
Kemp et al., Ann. Rev. Microbiol. 41, 181 (1987).
Ozaki et al., Cell 34, 815 (1983).
Galinski et al., Cell 48, 311 (1987).
Li et al., Chem. Absts. 110:55218 (1989).

*Primary Examiner*—Robert J. Hill, Jr.
*Assistant Examiner*—Nina Ossanna
*Attorney, Agent, or Firm*—Scott J. Meyer

[57] ABSTRACT

An *Entamoeba histolytica* specific cDNA clone which encodes an antigenic surface membrane protein possessing multiple tandem repeats and expression in *E. coli* is disclosed. This surface membrane protein is useful in a diagnostic assay for amebiosis.

1 Claim, 5 Drawing Sheets

```
                    10                    30                         50                              70
ORF1    MetPheAlaPheLeuLeuPheIleAlaPheThrSerAlaThrAsnIleIleLeuAspLeuAspGlnGluValLysAsp
        TCAATGTTCGCATTTTTATTGTTATTGCATTCACTAGTGCAACTAATATCATTCTTGATTGGATCAAGAAGTAAAAGAT 90                   110                        130                            150
        ThrAsnIleTyrGlyValPheLeuLysAsnGluAlaAlaSerProGluLysLeuGluGluAlaGluGluLysSerSer
        ACTAATATCTACGGTGTATTTCTTAAAGAACGAAGTCCTGAAAAGCTGAAGAAGCTGAAGAAAAGAGAAAAAAGTAGC 170                  190                        210                            230
        SerAlaLysProGluSerSerSerSerAsnGluAspAspAsnGluAlaSerSerGluLysAlaSerSerAsnSerGlu
        TCAGCAAAAACCAGAATCAAGTTCAAATGAAGATGATGAAGATAATGAAGCAAGTTCAAGTGAAAAAGCAAGTAACTCAGAA
                                                    MetLysIleMetLysMetMetLysLysGlnValIleThrGlnAs
ORF2
                    250                  270                        290                            310
        SerSerSerAspLysProAspAsnLysProGluAlaSerSerSerAspLysProGluAlaSerSerSerAspLysPro
        TCAAGTTCAAGTGATAAACCAGATAATAAACCAGAAGCAAGTTCAAGTTCAAGTGATAAGCCAGAAGCAAGTTCAAGTCCA
        nGlnAlaGlnGlnLysGlnValIleAsnGlnIleIleAsnGlnValGlnValIleAsnGlnLysGlnValGlnValIleAsnGl 330                  350                        370                            390
        AspAsnLysProGluAlaSerSerSerAspLysProAspAsnLysProGluAlaSerSerSerAspLysProAspAsnLys
        GATAATAAACCAGAAGCAAGTTCAAGTTCAAGTGATAAACCAGATAATAAACCAGAAGCAAGTTCAAGTTCAAGTGATAAACCAGATAATAAA
        nIleIleAsnGlnIleIleAsnGlnValGlnValIleAsnGlnLysGlnValGlnValIleAsnGlnIleIleAs
```

FIG. 2A

```
      410                430                450                 470
ProGluAlaAla SerSerSerAspLysProGluAla SerSerSerAspLysProAspAsnLys ProAspAsnLysProGluAla
CCAGAAGCAAGTTCAAGTCAAGTGATAAAACCAGAAGCAAGTCAAGTGATAATAAACCAGATAATAAACCAGAAGCA
nGlnLysGlnValGlnValIleAsnGlnIleIleAsnGlnValIleAsnGlnIleIleAsnGlnIleIleAsnGlnLysGl 490                510                530                 550
SerSerThrAsnLysProGluAla SerSerSerAspLysProGluAla SerSerThrAsnLysProGluAla SerSerThr
AGCTCAACTAATAAACCAGAAGCAAGTCAACTAATAAACCAGAAGCAAGTCAACTAATAAACCAGAAGCAAGTCAACT
nAlaGlnLeuIleAsnGlnLys GlnAlaGlnLeuIleAsnGlnLys GlnAlaGlnLeuIleAsnGlnLys GlnAlaGlnLe 570                590                610                 630
AsnLysProGluAla SerSerThrSerAsnSerAsnAspLysSerGlyLysSerSerAspAsnAsnAsnLeuAsp
AATAAACCAGAAGCAAGTCAACTAATTCAACTAGTAATCAGAGGAAGTAGTCAGATAACGATAATAATAACCTTGAT
uIleAsnGlnLys GlnAlaGlnLeuIleAsnGlnMetIleGlnIleIleThrIleIleIleThrLeuMe 650                670               690                710
AlaAlaAlaSerSerProPheIleValPheCysAlaIlePheIleIleAlaIleIleIlePheEnd
GCTGCATCAAGTCCATTCATTGTTTTCTGTGCTATCATTGCTATCATCTTCTAAATGAGTTATTGACTTT
tLeuHisGlnValHisSerLeuPheSerValLeuSerLeuEnd
```

FIG. 2A (CONT.)

SREHP
CSP

■ HYDROPHOBIC REGION  ▨ CHARGED AMINO ACIDS  ▨ DODECAPEPTIDE REPEATS  ▨ OCTAPEPTIDE REPEATS

FIG. 2B

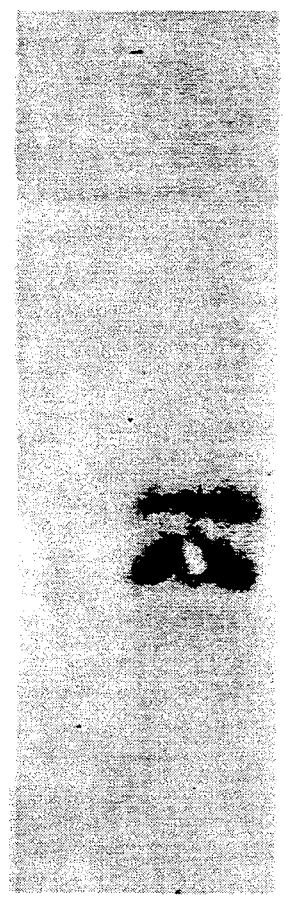
S  P
HMI:IMSS   LAREDO
FIG. 4

ENTAMOEBA HISTOLYTICA DIAGNOSTIC ASSAY

This is a division of application Ser. No. 07/516,388, filed Apr. 30, 1990, now U.S. Pat. No. 5,130,417.

BACKGROUND OF THE INVENTION

This invention relates to an immunogenic protein and cDNA which codes for said protein. More particularly, the invention is concerned with a surface membrane antigen of Entamoeba histolytica and a E. histolytica specific cDNA clone which encodes a serine rich E. histolytica protein.

The protozoan pathogen Entamoeba histolytica is a major cause of debilitating illness and death worldwide, infecting more than 500,000,000 people, and causing an estimated 50,000,000 cases of diarrhea, and 50,000 deaths yearly [Walsh in Aembiasis, Human Infection by Entamoeba histolytica, ed. Ravdin, J. I., John Wiley & Sons, Inc. New York, N.Y., pp. 93-105 (1988)]. There is an urgent need for a vaccine which could prevent the establishment of E. histolytica infection, or the development of invasive disease. Previous studies in animal models have demonstrated that immunity to E. histolytica infection can be produced by immunization with E. histolytica lysates [Ghadirian et al., Am. J. Trop. Med. Hyg. 29, 779-784 (1980); Krupp, Am. J. Trop. Med. Hyg. 23, 355-360 (1974); and Swartzwelder and Avant, Am. J. Trop. Med. Hyg. 567-575 (1952)]. However, the difficulty in obtaining large quantities of trophozoites, and the relatively crude nature of the immunizing preparations have severely limited the scope of these prior studies.

Recently, genomic differences between pathogenic and nonpathogenic E. histolytica have been reported by Tannich et al., Proc. Natl. Acad. Sci. USA 86, 5118-5122 (1989). These scientists utilized antibody screening and reported an amino acid sequence derived from a partial cDNA clone. No putative initiator methionine was found and no nucleotide data was reported by them. Nor are any tandem repeats or other characterization of the partial amino acid sequence provided by Tannich et al. No biological role for the Tannich et al protein is found in their report; instead, the paper is completely directed to the use of their partial cDNA clone to detect genomic differences between E. histolytica strains. However, Southern blotting with actin (a conserved protein, found in almost all organisms, and originally isolated by another scientific group) shows the same ability to differentiate between strains of E. histolytica as their probe, thereby suggesting that their probe is not unique in its ability to differentiate between E. histolytica strains.

BRIEF DESCRIPTION OF THE INVENTION

In accordance with the present invention an Entamoeba histolytica specific cDNA clone which encodes an antigenic surface membrane protein possessing multiple tandem repeats has been isolated and expressed in E. coli.

In particular, differential hybridization screening was used to isolate an illustrative E. histolytica specific cDNA clone, designated c1. The cDNA was found to encode a serine rich E. histolytica protein (hereinafter also referred to as SREHP) containing multiple tandem repeats. The structural motif of SREHP resembles some of the repetitive antigens of malarial species, especially the circumsporozoite proteins. A recombinant trpE fusion protein containing the tandem repeats of SREHP was recognized by immune serum from a patient with amebiasis, demonstrating that SREHP is a naturally immunogenic protein. An antiserum raised against the recombinant fusion protein specifically bound to two distinct bands with apparent molecular weights of 46 and 52 kd in a crude preparation of E. histolytica trophozoite membranes. This antiserum also inhibited E. histolytica trophozoite adhesion to Chinese Hamster Ovary cells in vitro. These properties suggest that SREHP plays a role in a key part (adhesion) of E. histolytica pathogenesis. SREHP also can be used as the target antigen in a serologic test for invasive amebiasis.

The recombinant trpE fusion protein is constructed by fusing the SREHP or a fragment thereof which contains at least the tandem repeats to the N-terminal two-thirds of the trpE gene of E. coli. This fusion can be carried out by conventional procedures such as described by Hardy and Strauss, J. Virol. 62(3), 998-1007 (1988), for making a fusion of polypeptides of Sindbis virus and the N-terminal two-thirds of the trpE gene of E. coli.

The ability to isolate E. histolytica specific genes, and to express those genes in E. coli, is important to medical science in studying the molecular basis of E. histolytica pathogenesis, and for development of vaccines and diagnostics.

The illustrative c1 cDNA sequence consists of 722 nucleotides and contains two open reading frames, designated ORF1 and ORF2. ORF1 contains a continuous open reading frame from a putative initiator methionine beginning at nucleotide 4 to a TAA termination at nucleotide 703. ORF2 has a most 5'methionine at nucleotide 188 and terminates at nucleotide 689. The cDNA sequence encodes a 25 kDa protein of 233 amino acids. Since serine constituted 52 of the 233 amino acids, the derived amino acid sequence of ORF1 is referred to as the serine rich E. histolytica protein (SREHP). By comparison, the derived 167 amino acid sequence of ORF2 is serine poor. The c1 cDNA nucleotide sequence and the two respective amino acid sequences encoded by PRF1 and ORF2 are as follows. The nucleotides and amino acids are numbered on the right.

| c1 cDNA | | | | | |
|---|---|---|---|---|---|
| TCAATGTTCG | CATTTTTATT | GTTTATTGCA | TTCACTAGTG | CAACTAATAT | 50 |
| CATTCTTGAT | TTGGATCAAG | AAGTAAAAGA | TACTAATATC | TACGGTGTAT | 100 |
| TTTTAAAGAA | CGAAGCTAGT | CCTGAAAAGC | TTGAAGAAGC | TGAAGAAAAA | 150 |
| GAAAAAAGTA | GCTCAGCAAA | ACCAGAATCA | AGTTCAAATG | AAGATAATGA | 200 |
| AGATGATGAA | GATGAAAAAG | CAAGTTCAAG | TGATAACTCA | GAATCAAGCT | 250 |
| CAAGTGATAA | ACCAGATAAT | AAACCAGAAG | CAAGTTCAAG | TGATAAACCA | 300 |
| GAAGCAAGTT | CAAGTGATAA | ACCAGATAAT | AAACCAGAAG | CAAGTTCAAG | 350 |
| TGATAAACCA | GATAATAAAC | CAGAAGCAAG | TTCAAGTGAT | AAACCAGATA | 400 |
| ATAAACCAGA | AGCAAGTTCA | AGTGATAAAC | CAGATAATAA | ACCAGAAGCA | 450 |

-continued

| | | | | | |
|---|---|---|---|---|---|
| AGCTCAAGTG | ATAAACCAGA | TAATAAACCA | GAAGCAAGCT | CAACTAATAA | 500 |
| ACCAGAAGCA | AGCTCAACTA | ATAAACCAGA | AGCAAGCTCA | ACTAATAAAC | 550 |
| CAGAAGCAAG | CTCAACTAAT | AAACCAGAAG | CAAGCTCAAC | TAGTAATTCA | 600 |
| AATGATAAAT | CAGGAAGTAG | TTCAGATAAC | GATAATAATA | ACCTTGATGC | 650 |
| TGCATCAAGT | CCATTCATTG | TTTTCTGTGC | TATCATTATA | GCTATCATCT | 700 |
| TCTAAATGAG | TTATTTGACT | TT | | | 722 |

ORF1

| | | | | | | | | | | | | | | | |
|---|---|---|---|---|---|---|---|---|---|---|---|---|---|---|---|
| Met | Phe | Ala | Phe | Leu | Leu | Phe | Ile | Ala | Phe | Thr | Ser | Ala | Thr | Asn | 15 |
| Ile | Ile | Leu | Asp | Leu | Asp | Gln | Glu | Val | Lys | Asp | Thr | Asn | Ile | Tyr | 30 |
| Gly | Val | Phe | Leu | Lys | Asn | Glu | Ala | Ser | Pro | Glu | Lys | Leu | Glu | Glu | 45 |
| Ala | Glu | Glu | Lys | Glu | Lys | Ser | Ser | Ser | Ala | Lys | Pro | Glu | Ser | Ser | 60 |
| Ser | Asn | Glu | Asp | Asn | Glu | Asp | Asp | Glu | Asp | Glu | Lys | Ala | Ser | Ser | 75 |
| Ser | Asp | Asn | Ser | Glu | Ser | Ser | Ser | Ser | Asp | Lys | Pro | Asp | Asn | Lys | 90 |
| Pro | Glu | Ala | Ser | Ser | Ser | Asp | Lys | Pro | Glu | Ala | Ser | Ser | Ser | Asp | 105 |
| Lys | Pro | Asp | Asn | Lys | Pro | Glu | Ala | Ser | Ser | Ser | Asp | Lys | Pro | Asp | 120 |
| Asn | Lys | Pro | Glu | Ala | Ser | Ser | Ser | Asp | Lys | Pro | Asp | Asn | Lys | Pro | 135 |
| Glu | Ala | Ser | Ser | Ser | Asp | Lys | Pro | Asp | Asn | Lys | Pro | Glu | Ala | Ser | 150 |
| Ser | Ser | Asp | Lys | Pro | Asp | Asn | Lys | Pro | Glu | Ala | Ser | Ser | Thr | Asn | 165 |
| Lys | Pro | Glu | Ala | Ser | Ser | Thr | Asn | Lys | Pro | Glu | Ala | Ser | Ser | Thr | 180 |
| Asn | Lys | Pro | Glu | Ala | Ser | Ser | Thr | Asn | Lys | Pro | Glu | Ala | Ser | Ser | 195 |
| Thr | Ser | Asn | Ser | Asn | Asp | Lys | Ser | Gly | Ser | Ser | Ser | Asp | Asn | Asp | 210 |
| Asn | Asn | Asn | Leu | Asp | Ala | Ala | Ser | Ser | Pro | Phe | Ile | Val | Phe | Cys | 225 |
| Ala | Ile | Ile | Ile | Ala | Ile | Ile | Phe | | | | | | | | 233 |

ORF2

| | | | | | | | | | | | | | | | |
|---|---|---|---|---|---|---|---|---|---|---|---|---|---|---|---|
| Met | Lys | Ile | Met | Lys | Met | Met | Lys | Met | Lys | Lys | Gln | Val | Gln | Val | 15 |
| Ile | The | Gln | Asn | Gln | Aln | Gln | Val | Ile | Asn | Gln | Ile | Ile | Asn | Gln | 30 |
| Lys | Gln | Val | Gln | Val | Ile | Asn | Gln | Lys | Gln | Val | Gln | Val | Ile | Asn | 45 |
| Gln | Ile | Ile | Asn | Gln | Lys | Gln | Val | Gln | Val | Ile | Asn | Gln | Ile | Ile | 60 |
| Asn | Gln | Lys | Gln | Val | Gln | Val | Ile | Asn | Gln | Ile | Ile | Asn | Gln | Lys | 75 |
| Gln | Val | Gln | Val | Ile | Asn | Gln | Ile | Ile | Asn | Gln | Lys | Gln | Ala | Gln | 90 |
| Val | Ile | Asn | Gln | Ile | Ile | Asn | Gln | Lys | Gln | Ala | Gln | Leu | Ile | Asn | 105 |
| Gln | Lys | Gln | Ala | Gln | Leu | Ile | Asn | Gln | Lys | Gln | Ala | Gln | Leu | Ile | 120 |
| Asn | Gln | Lys | Gln | Ala | Gln | Leu | Ile | Asn | Gln | Lys | Gln | Ala | Gln | Leu | 135 |
| Val | Ile | Gln | Met | Ile | Asn | Gln | Glu | Val | Val | Gln | Ile | The | Ile | Ile | 150 |
| Ile | Thr | Leu | Met | Leu | His | Gln | Val | His | Ser | Leu | Phe | Ser | Val | Leu | 165 |
| Ser | Leu | | | | | | | | | | | | | | 167 |

In order to demonstrate a practical utility of the novel SREHP of the invention, 90 sera from 88 patients were examined by Western blotting for the presence of antibodies to this serine rich *E. histolytica* protein. The target antigen was a recombinant trpE fusion protein containing most of the SREHP sequence, including the tandem repeats. Among patients with amebic liver abscess from Durban, San Diego, and Mexico, 49 of 61, (79%) had antibodies to SREHP. In contrast only 1 patient out of 24 (4%) without acute invasive amebiasis had antibodies to SREHP. The specificity of anti-SREHP antibodies in the detection of acute invasive amebiasis was most marked when analyzed in the patients from Durban, where 11 of 12 (92%) patients seropositive for SREHP had acute invasive amebiasis, versus 17 of the 26 (65%) patients positive by agar gel diffusion. The use of a serologic test based on the recombinant SREHP fusion protein thus is deemed to be a useful adjunct to the diagnosis of acute invasive amebiasis in endemic regions.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

BRIEF DESCRIPTION OF THE DRAWINGS

FIG. 2(A) shows the nucleotide and derived amino acid sequence of the c1 cDNA. The derived amino acid sequence for both ORF1 and ORF2 is shown. The dodecapeptide and octapeptide repeats in both ORF are boxed. FIG. 2(B) shows the general structure of SREHP according to the invention compared to the circumsporozoite protein (CSP) of *Plasmodium knowlesi* as reported by Ozaki et al., Cell 34, 815–822 (1983). The *P. knowlesi* dodecapeptide repeat consists of Gly-Gln-Pro-Gln-Ala-Gln-Gly-Asp-Gly-Ala-Asn-Ala.

FIG. 4 provides identification of the native HM1:IMSS SREHP and shows Western blot analysis of the supernatant (S) and pellet (P) from the 100,000×g centrifugation of HM1:IMSS trophozoite lysates, and whole Laredo lysates, using antiserum against the SREHP fusion protein. Molecular weight standards in kDa are indicated at the right.

Figure 1:
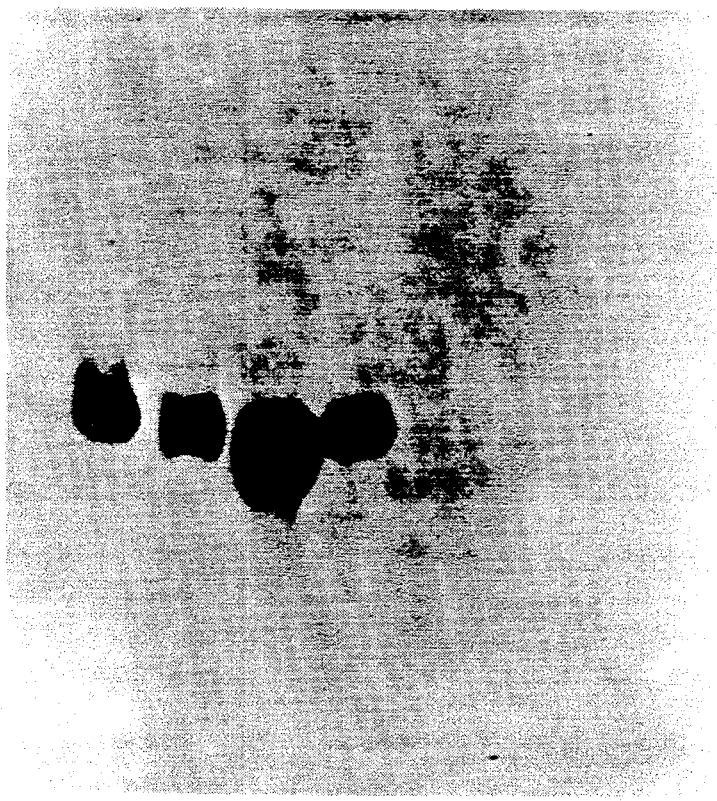
FIG. 1 shows the Northern blot of amebic RNA probed with the illustrative c1 clone of the invention. Lane 1, Molecular weight standards; lane 2, HM1:IMSS; lane 3, HK9; lane 4, NIH:200; lane 5, Rahman; lane 6, Laredo; lane 7, *E. invadens*; lane 8, *E. moshkovskii*; lane 9, Molecular weight standards.

Standard biochemical nomenclature is used herein in which the nucleotide bases are designated as adenine (A); thymine (T); guanine (G); and cytosine (C). Corresponding nucleotides are, for example, deosyadenosine-5'-triphosphate ((dATP). As is conventional for convenience in the structural representation of a DNA nucleotide sequence, only one strand is usually shown in which A on one strand connotes T on its complement and G connotes C.

Amino acids are shown either by their common three letter or one letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

In order to illustrate specific preferred embodiments of the invention in further detail, the following exemplary laboratory preparative work was carried out although it will be understood that the invention is not limited to these specific examples.

EXAMPLE 1

This example illustrates the isolation of the *E. histolytica* specific cDNA clone, designated c1, and the characterization and properties of the SREHP.

MATERIALS AND METHODS

*E. histolytica* isolates and culture conditions. The *E. histolytica* strain HM1:IMSS is virulent in vivo and in vitro [Li et al, *Infect. Immun*, 57, 8–12 (1989); Mattern and Keister, *Am. J. Trop. Med. Hyg.* 27, 882-887 (1977)]. The *E. histolytica*-like Laredo strain was isolated from a patient with diarrhea [Diamond, *J. Parasitol*, 54, 1047-1056 (1968)], but is avirulent in in vitro cytoxicity assays and in animal models. Both strains were grown axenically in TYI-S-33 media by conventional procedure as described previously by Diamond et al., *Trans. R. Soc. Trop. Med. Hyg.* 4, 431-432 (1978).

Construction and screening of a HM1:IMSS cDNA library. Total cellular RNA was isolated from exponentially growing HM1:IMSS and Laredo trophozoites using the method of Chirgwin et al., *Biochemistry* 18, 5294-5299 (1979). Poly-(A)+-RNA was purified by chromatography on oligo(dT)-cellulose [Maniatis et al., *Molecular Cloning: A Laboratory Manual* (Cold Spring Harbor Lab., Cold Spring Harbor, N.Y. (1982)], and used to prepare double stranded cDNA [Gubler and Hoffman, *Gene* 25, 263-269, (1983)]. The double stranded cDNA was C-tailed using the enzyme terminal deoxynucleotidyl transferase, and annealed with G-tailed PstI digested pUC13 [Villa-Komaroff et al., *Proc. Nat. Acad. Sci. USA* 75, 3727-3731 (1978)]. The chimeric plasmid was used to transform DH-5 *E. coli* [Hanahan, *J. mol. Biol.* 66, 557-580 (1983), generating a cDNA library containing 50,000 recombinants. Replica filters of 10,000 recombinants were probed with radiolabeled single stranded cDNA from HM1:IMSS or the non-pathogenic, *E. histolytica*-like, Laredo strain, respectively.

Northern blot analysis. Northern blots were prepared after 20 μg samples of total cellular RNA were subjected to electrophoresis through 1.5% agarose gels containing formaldehyde [Thomas, *Proc. Nat. Acad. Sci. USA* 77, 5201-5205 (1980)]The Northern blots were probed with cDNA labeled with [α-$^{32}$P]ATP to a specific activity of 1000 cpm/pg by the random primer method of Feinberg and Vogelstein, *Anal. Biochem.* 132, 6-13 (1983). The hybridization and washing conditions were identical to those itemized by Li et al., *Proc. Nat. Acad. Sci. USA*, 83, 5779-5783 (1986), except the last three washes were done at 60° C. Autoradiographs were exposed for 24 hours.

Nucleotide sequence analysis. The cDNA clones were sequenced using the technique of Maxam and Gilbert, *Methods Enzymol.* 65, 499–560 (1980). The cDNA sequence of clone c1 was completed using primer extension as described by Heuckeroth et al., *J. Biol. Chem.* 262, 9709-9717 (1987), utilizing the oligonucleotide TTCAGGACTAGCTTCGTTCTT derived from the sequence of c1.

Construction of trpE hybrid gene fusions. The pATH2 and pATH3 plasmids [described by Hardy and Strauss, *J. Virology* 62, 998-1007 (1988)] were used to express both open reading frames of the c1 cDNA clone in *E coli*, as trpE fusion proteins. The HindIII-SmaI fragment of c1 (containing nucleotides 128-722 and a portion of the PUC13 polylinker region) was ligated into the HindIII site and the ClaI site (which had been made blunt-ended with Klenow DNA polymerase) of pATH3 to construct pORF1. The HindIII-SmaI fragment was ligated into the HindIII and blunt ended ClaI sites of pATH2 to construct pORF2.

Expression and partial purification of the trpE fusion proteins. The trpE fusion proteins were expressed as described by Hardy and Strauss, supra, except the bacteria were harvested after incubation with γ-indoleacrylic acid for 24h. An insoluble protein fraction was prepared from pelleted cells as previously described by Hardy and Strauss, supra, to partially purify the trpE proteins. The yield of fusion protein as determined by discontinuous SDS-PAGE using molecular mass standards for comparison was 15 to 30 μg of protein per ml of culture.

Immunizations. Polyclonal rabbit serum directed against HM1:IMSS trophozoites was obtained by immunizing New Zealand White Rabbits subcutaneously with a preparation of 2×10$^6$ HM1:IMSS trophozoites suspended in complete Freunds Adjuvant. Booster immunizations were performed using the same preparation in incomplete Freunds Adjuvant. Serum was first collected two weeks after the initial booster injection, and subsequently two weeks after each consecutive booster.

Gel purification of the fusion proteins, and immunization of female New Zealand White Rabbits with fusion proteins, was performed exactly as described by Hardy and Strauss, supra, using 75 to 100 μg of protein per injection. Serum was collected from each rabbit before immunization to serve as a control, then 6 weeks after the initial immunization (two weeks after the first booster), and two weeks after each consecutive booster.

Western blots. For Western blotting of the fusion proteins with *E. histolytica* immune human and rabbit serum, the insoluble protein fraction of bacterial cells from 0.3 ml cultures was separated by 10% SDS-PAGE under reducing conditions, then transferred to nitrocellulose. Blots were reacted with immune or pre-immune serum diluted 1/500, and immunoglobulin binding detected using $^{125}$I labeled staphlococcal protein-A. Blots were autoradiographed for 12 hr.

For Western blotting of amebic lysates with antiserum against recombinant proteins, $5 \times 10^6$ trophozites from 72 hr cultures were washed 2' in phosphate buffered saline (PBS), then suspended in 2 ml of PBS containing 5 mM EDTA/2 mM leupeptin/5 mM N-ethylmaleimide/2 MM phenylmethylsulfonyl fluoride/2 mM benzamidine/5 mM trans-epoxysuccinyl-L-leucylamido(4-guanidino)-butane (E-64). The trophozoites were lysed by sonication, and homogenates of the HM1:IMSS trophozoites were centrifuged at $100,000 \times$ g for 1 hr. Aliquots of the $100,000 \times$ g supernatant and pellet fraction corresponding to $10^5$ trophozoites were denatured, separated by 10% SDS-PAGE under reducing conditions, then transferred to nitrocellulose. Blots 5 were reacted with a 1/1000 dilution of rabbit antiserum to the fusion protein; subsequent steps were performed as described above.

Adherence of $^3$H-thymidine labeled *E. histolytica* trophozoites to monolayers of 1021 Chinese Hamster Ovary Cells. These tests were performed by conventional procedures as described previously by Li et al., *J. Exp. Med.* 167, 1725–1730 (1988). 0.25 ml of media with or without the antisera to be tested were added to the monolayers immediately before addition of 0.25 ml of trophozoites suspended at $8 \times 10^5$ cells/ml. A 1:10 dilution of each of the antisera tested was used. Duplicate wells were used for each assay. Data are presented as the % of trophozoite adherence seen in the media control group±standard deviation.

RESULTS

Isolation of a cDNA clone from the pathogenic *E. histolytica* HM1:IMSS strain. 10,000 recombinants from the pUC13 cDNA library derived from HM1:IMSS mRNA were screened with radiolabeled single stranded cDNA transcribed from poly A+ RNA from HM1:IMSS or the non-pathogenic, *E. histolytica*-like Laredo strain, respectively. Four unique clones that hybridized to HM1:IMSS cDNA, but not to Laredo cDNA were isolated. The characterization of one of the clones, c1, is described in detail herein.

Analysis of c1 gene expression by RNA blot hybridization. The expression of the gene corresponding to the c1 clone was examined by blot hybridization studies of RNA isolated from 4 *E. histolytica* strains, Laredo, *Entamoeba invadens*, and *Entamoeba moshkovskii* (FIG. 1). The c1 clone hybridized with a 0.8 kb species in all four axenic strains of *E. histolytica*, but did not hybridize with RNA from Laredo, or the two non-*E. histolytica* sp., *E. invadens*, and *E. moshkovskii*. When a Southern blot of EcoR1 digested genomic DNA from the same ameba was probed with the c1 clone, a 4.4 kb fragment was noted in all four *E. histolytica* strains, but not in Laredo, *E. invadens*, or *E. moshkovskii*. The results from RNA and DNA hybridization tests indicate that the gene corresponding to the c1 clone is present and expressed only in the *E. histolytica* strains, and not in the other *Entamoeba* sp. surveyed.

Nucleotide sequence of the c1 cDNA clone. The c1 cDNA sequence consisted of 722 nucleotides (FIG. 2A), and contained two open reading frames, which were designated ORF1 and ORF2. ORF1 contained a continuous open reading frame from a putative initiator methionine beginning at nucleotide 4 to a TAA termination at nucleotide 703. Beginning at nucleotide 247 ORF1 contained a stretch of 36 nucleotides encoding the dodecapeptide Ser-Ser-Ser-Asp-Lys-Pro-Asp-Asn-Lys-Pro-Glu-Ala. After a 24 nucleotide space encoding a similar octapeptide, the dodecapeptide was tandemly repeated 5 times, followed by 4 repeats of an octapeptide, Ser-Ser-Thr-Asn-Lys-Pro-Glu-Ala. The nucleotide sequence of the dodecapeptide repeats was highly conserved, with the only difference being the use of C or U in the third position of the codon for the first serine of each repeat. The repeated octapeptide represents a truncated version of the dodecapeptide, with a single nucleotide change substituting a threonine for the third serine, and nucleotides encoding both Asp residues, and one of the Lys and Pro residues absent. Serine constituted 52 of the 233 amino acids, hence the derived amino acid sequence of ORF1 is referred to as the serine rich *E. histolytica* protein (SREHP). Three contiguous serine residues were part of the dodecapeptide repeats, and were found in five other locations in the protein. The repeats were preceded by a highly charged region consisting of multiple lysine, glutamate, and aspartate residues. ORF1 terminated with 54 nucleotides encoding primarily hydrophobic amino acids, consistent with a possible membrane insertion or spanning region. The initial 13 amino acids of the NH2-terminus possess some of the characteristics of a eukaryotic signal sequence as defined by the algorithm of von Heinje, *Nuc. Acids Res.* 14, 4683–4690 (1986), with a possible cleavage site between the Ala at position 13 and Thr at position 14. The sequence differed from other signal sequences in the absence of one or more charged amino acids (n-domain) before the hydrophobic core (h-domain).

The second ORF, ORF2, possessed 5 methionine codons at the 5' end, with the most 5' beginning at nucleotide 188 (FIG. 2A). ORF2 also encoded a tandemly repeated dodecapeptide, Gln-Val or Ala-Gln-Val-Ile-Asn-Gln-Ile-Ile-Asn-Gln-Lys, which began at nucleotide 245, and had a pattern of repeats similar to ORF1, with 5 additional dodecapeptide repeats followed by 4 repeats of an octapeptide, Gln-Ala-Gln-Leu-Ile-Asn-Gln-Lys. ORF2 terminated with a relatively hydrophobic region.

Figure 3A:
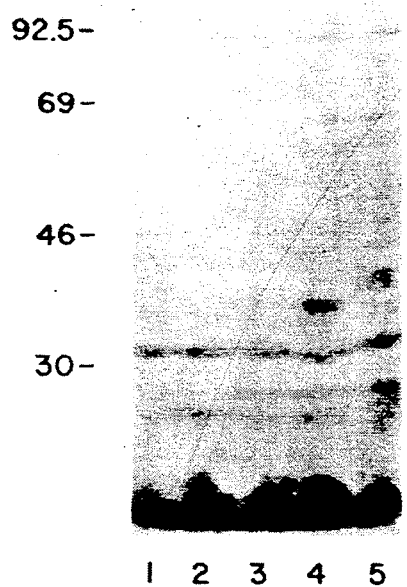
FIG. 3 (A through D) shows the Western blotting of trpE fusion proteins with normal human serum (A), immune serum from a patient with amebic liver abscess (B), pre-immune rabbit serum (C), and serum from a rabbit immunized with HM1:IMSS trophozoites (D), performed as described in Materials and Methods, hereinafter. The insoluble protein fraction containing the trpE fusion proteins were prepared as described in Materials and Methods from induced bacteria containing: Lane 1, pORF2 (encoding the Gln-Val-Gln-Val-Ile-Asn-Gln-Ile-Ile-Asn-Gln-Lys repeats); lane 2, pORF1 (encoding a portion of SREHP including the Ser-Ser-Ser-Asp-Lys-Pro-Asp-Asn-Lys-Pro-Glu-Ala repeats); lane 3, pATH2 vector only; lane 4, pATH3 vector only; lane 5, lacking plasmid. Molecular weight standards in kDa are indicated at the left of each panel.
Figure 3B:
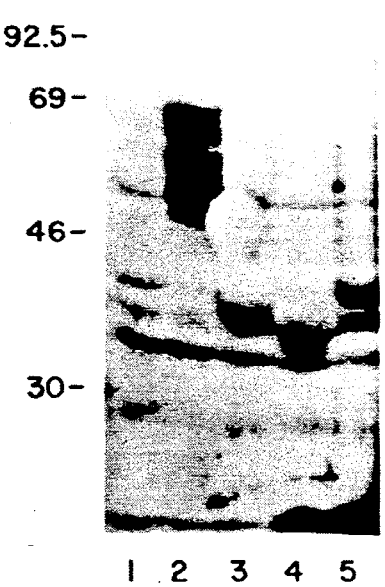
Figure 3C:
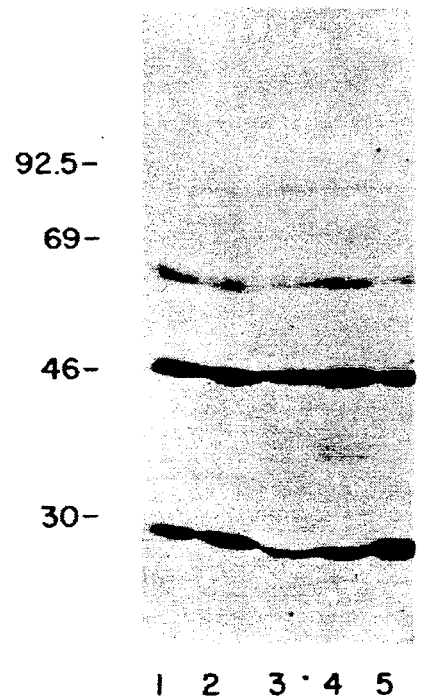
Figure 3D:
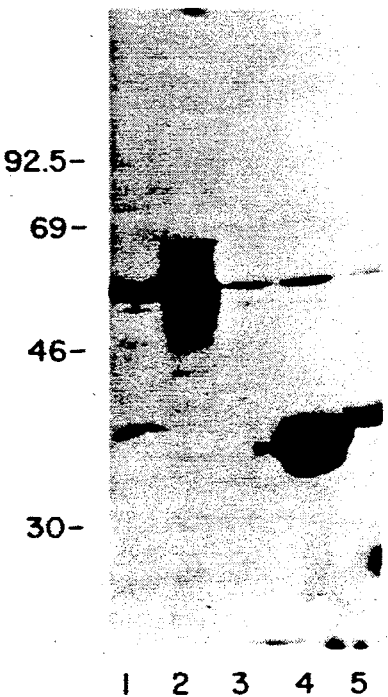

A search of the Genbank and NBRF data banks revealed no sequences with significant homology with either the nucleotide or derived amino acid sequences from c1. In addition, the derived amino acid sequences from c1 differ from the partial sequence of the *E. histolytica* cDNA clone recently reported by Tannich et al., *Proc. Natl. Acad. Sci. USA* 86, 5118–5122 (1989). Tandem repeats have been found in antigens from other parasites, but are most prominent among the antigens of malaria species [Kemp et al., *Ann. Rev. Microbiol.* 41, 181–208 (1987)]. The primary structural motif of SREHP is similar to the repetitive antigens of malarial species, most notably the circumsporozoite proteins et al, supra, and Ozaki et al., *Cell* 34, 815–822 (1983)]. Circumsporozoite proteins cover the surface of the sporozoite stage of the malaria parasite, range in size from 40 to 60 kDa, and contain a species specific pattern multiple tandem repeats. The predicted structure of the P. knowlesi circumsporozoite protein consists of a hydrophobic $NH_2$ terminal region followed by a series of tandemly repeated amino acids flanked by two domains containing predominantly charged amino acids, and concluding with a COOH-terminal region, consisting of a hydrophobic anchor region (FIG. 2B) [Ozaki et al., supra]. The predicted structure of SREHP consists of a hydrophobic $NH_2$-terminal region, followed by a region containing primarily charged amino acids, followed by tandemly repeated amino acids, and ends with a COOH-terminal hydrophobic region (FIG. 2B). In the $NH_2$-terminal charged area of the P. knowlesi circumsporozoite protein, 27 of the 48 amino acid residues are charged (primarily lysine and glutamate residues [Ozaki, supra.], whereas 21 of the 36 residues are charged (primarily lysine, glutamate, and aspartate) in the comparable $NH_2$-terminal region of SREHP. Unlike circumsporozoite proteins SREHP does not possess a second COOH-terminal group of charged amino acids. An additional similarity between SREHP and circumsporozoite proteins lies in the amino acids utilized in the repeating units. Circumsporozoite protein repeats appear to be derived from a repertoire of 8 amino acids, Ala, Pro, Gly, Asn, Gln, Asp, Arg, and Glu [Galinski et al, Cell 48, 311-319 (1987)]. Five of these 8 amino acids, Ala, Pro, Asn, Asp, and Glu, are among the 7 amino acids which make up the dodecapeptide repeats of SREHP.

c1 cDNA encodes a naturally immunogenic E. histolytica protein. Since it was not known which of the ORF of c1 were translated in E. histolytica, both open reading frames of c1 in E. coli using the trpE containing vectors pATH2 and pATH3 were expressed. Constructs, pORF1 and pORF2, containing most of the sequence of the c1 insert fused in the appropriate reading frame to the N-terminal two-thirds of the E. coli trpE gene were expressed. Coomassie blue staining of SDS-PAGE separated insoluble pellets from cells containing the pORF1 or pORF2 vector which had been induced to produce trpE by γ-indoleacrylic acid revealed fusion proteins with molecular weights of approximately 60 kDa (the prediced molecular weights for the fusion proteins encoded by ORF1 and ORF2 are 57 kDa and 59 kDa respectively). To determine whether either of the ORF of c1 produced a naturally immunogenic e. histolytica protein, Western blotting was performed (FIG. 3). Immune serum from a patient with amebic liver abscess and serum from a rabbit immunized with HM1:IMSS trophozoites both bound to a series of bands, (highest MW approximately 60 kDa) in bacteria expressing the fusion protein (predicted MW 57 kDa) encoded by pORF1 (FIG. 3B and D, lane 2). Immune serum did not bind to the fusion protein encoded by pORF2. Control human serum and preimmune rabbit serum did not bind either of the fusion proteins (FIG. 3A and C), In subsequent studies it was found that serum from 25 additional patients with invasive amebiasis also bind the fusion protein produced by pORF1. It has been confirmed that the recombinant protein recognized by immune serum contains the tandemly repeated peptides encoded by ORF1 by demonstrating that antiserum to a synthetic peptide containing the dodecapeptide repeat Ser-Ser-Ser-Asp-Lys-Pro-Asp-Asn-Lys-Pro-Glu-Ala binds the recombinant protein.

SREHP is a membrane protein. In order to determine whether SREHP is associated with a membrane fraction of E. histolytica, HM1:IMSS trophozoites were lysed, then spun at 100,000× g and loaded onto SDS-PAGE as a supernatant and pellet fraction. As shown in lo the Western blot (FIG. 4), the anti-SREHP fusion protein antiserum specifically bound to two distinct bands at molecular weight 46 kDa and 52 kDa in the 100,000× g pellet fraction. Little binding was detected in the 100,000× g supernatant suggesting the native SREHP is primarily membrane bound. This finding is consistent with the primary structure data. The anti-SREHP fusion protein antiserum showed no binding to any species in whole Laredo lysates, suggesting SREHP is E. histolytica-specific. It is presently unclear why antiserum to the recombinant SREHP fusion protein detects two species with molecular weights approximately twice that predicted from the derived amino acid sequence of the SREHP cDNA (25 kDa) in the E. histolytica lysates. The results of the Northern blotting study (FIG. 1) demonstrated that the size of the c1 clone (722 nucleotides) is close to the size of the SREHP transcript (approximately 800 nucleotides) suggesting that most, if not all, of the coding region should be contained in the c1 clone. Hence it is unlikely that the discrepancy in size results from additional amino acids, and more likely it is secondary to post-translational modifications. Antiserum to the fusion protein encoded by pORF2 showed no binding to HM1:IMSS trophozoite lysates by Western blotting. Thus the results do not demonstrate the existence of a HM1:IMSS trophozoite protein encoded by c1 ORF2. One cannot exclude the possibility that ORF2 might be translated in the cyst form of the parasite.

Antiserum to the SREHP fusion protein inhibits E. histolytica HM1:IMSS adhesion to Chinese Hamster Ovary Cells. The adherence of E. histolytica HM1:IMSS trophozoites to a panel of Chinese Hamster Ovary cells was previously studied and it was shown that trophozoites adhere best to the 1021 Chinese Hamster Ovary cell line, Li et al, J. Exp. Med. 167, 1725-1730 (1988). The ability of antiserum to the SREHP fusion protein to inhibit the binding of radiolabeled E. histolytica HM1:IMSS trophozoites to 1021 cells was evaluated. Antiserum to the SREHP fusion protein with preimmune serum, antiserum to the fusion protein encoded by pORF2, and a media control were compared. Antiserum to the SREHP fusion protein reduced the binding of HM1:IMSS trophozoites to 1021 cells to 30±2% of control levels (Table 1). Preimmune serum, and antiserum to the fusion protein encoded by pORF2, had no inhibitory effects. This finding suggests that SREHP is located on the trophozoite cell surface, and can play a role in E. histolytica adhesion. It is notable in this regard that a recent study by Rodriguez et al using a polyclonal antisera against total amebic proteins found that an E. histolytica protein of molecular weight 50 kDa was one of 7 E. histolytica proteins found on the surface of red blood cells incubated with trophozoites Rodriguez et al, Mol. Biochem. Parisitol. 37, 87-100 (1989)].

TABLE 1

Antiserum to the recombinant SREHP fusion protein inhibits the binding of HM1:IMSS trophozoites to the 1021 Chinese Hamster Ovary Cell line.

| SERA | % of Control Binding to 1021 Cells |
|---|---|
| Preimmune | 94 ± 25 |
| Anti-SREHP fusion protein | 30 ± 2 |

TABLE 1-continued

Antiserum to the recombinant SREHP fusion protein inhibits the binding of HM1:IMSS trophozoites to the 1021 Chinese Hamster Ovary Cell line.

| SERA | % of Control Binding to 1021 Cells |
|---|---|
| Anti-ORF2 fusion protein | 120 ± 25 |

Results are the means from 3 tests and are presented as the % of trophozoite adherence seen in the media control group ± standard deviation.

EXAMPLE 2

This example illustrates the use of the SREHP as a target antigen in a serologic test for invasive amebiasis.

INTRODUCTION

The serologic diagnosis of invasive amebiasis is problematic. The indirect hemagglutinin test (IHA) is sensitive for the detection of invasive amebic infection, but seropositivity can persist for years after infection [Krupp, J. Trop. Med. Hyg. 19, 57–62 (1970); Lobel and Kagen, Ann. Rev. Microb. 32, 329–47 (1978)]. Agar gel diffusion (AGD) and counter immune electrophoresis (CIE) offer improved detection of acute disease, but seropositivity may persist for six months or more after infection. [Lobel and Kagen supra; Krupp and Powell, Am. J. Trop. Med. Hyg. 20, 421–24 (1971); Juniper et al., Ibid. 21, 157–68 (1972); Jackson et al., Trans. Roy. Soc. Trop. Med. Hyg. 78, 342–45 (1984)]. Given these findings it is not surprising that in regions endemic for invasive amebiasis between 6 and 20% of healthy subjects will have positive serology, probably secondary to prior infection with pathogenic E. histolytica. [Lobel and Kagen, supra; Jackson et al., Lancet 1985; i:7-16–719.] This high background level of seropositivity in endemic areas can limit the usefulness of serology in the diagnosis of acute invasive disease.

SREHP appears to be present only in E. histolytica, and has a structure consisting of multiple tandem repeats, resembling the circumsprozoite proteins of malaria. In Example 1, above, it was demonstrated that serum from a patient with invasive amebiasis bound to a recombinant fusion protein containing the multiple tandem repeats encoded by the SREHP gene. This Example 2 provides further analysis of the serologic response to SREHP. The objectives were to examine the prevalence of antibodies to SREHP among patients with amebic liver abscess in two different endemic regions, and to determine whether the recombinant SREHP fusion protein might be useful in a serologic test for the diagnosis of invasive amebiasis. This Example 2 describes the finding that the presence of antibodies to SREHP has a high correlation with the presence of acute invasive amebiasis.

MATERIALS AND METHODS

Production of SREHP Fusion Protein. The pATH3 plasmid vector was used to express nucleotides 128 to 722 of the SREHP cDNA (containing the multiple tandem repeats) in E. coli as a 60 kDa trpE fusion protein as described in Example 1. A second, smaller open reading frame (ORF2), of the SREHP cDNA which does not appear to be expressed in E. histolytica trophozoites, was expressed in pATH2, and served as a control fusion protein for Western blotting. The fusion proteins were partially purified from bacteria induced to produce trpE as described in Example 1.

Western Blotting. For Western blotting the insoluble protein fractions from bacteria expressing the fusion proteins were separated by 10% SDS-PAGE under reducing conditions then transferred to nitrocellulose as described in Example 1. Blots were reacted with human serum samples to be tested at a 1:500 dilution, and immunoglobulin binding detected using $^{125}$I labeled staphylococcal protein-A. Blots were autoradiographed for 12 hr. Blots were read independently by four observers, (SLS, CKJ, AB, and EL). Criteria for a positive blot were binding to SREHP recombinant fusion protein, and minimal or no binding to the control ORF2 fusion protein.

Study Population. The characteristics of the study population are outlined in Table 2, below. 33 sera samples from Mexico City were obtained from 33 patients with the diagnosis of amebic liver abscess based on clinical presentation and positive serology. 14 samples were obtained from patients seen in San Diego, four with intestinal invasive amebic disease (3 colitis, 1 ameboma) and 9 with the diagnosis of amebic liver abscess (one patient had two separate episodes of amebic liver abscess with a serum sample provided from each episode), all with positive serology. 36 sera were obtained from 36 patients in Durban; this sample group was specifically selected in Durban and contained sera from patients with amebic liver abscess (17), and sera from patients with other illnesses (19), some of whom had positive AGD serology. Samples were either sent encoded, or the blots were read by observers with no knowledge of the clinical history. 2 sera, an acute and 1 yr convalescent serum, were examined from one patient from St. Louis who contracted an amebic liver abscess in Mexico, five sera from healthy people in St. Louis were included as negative controls.

RESULTS

A total of 90 sera from 88 patients were examined for the presence of antibodies to SREHP. Of the 61 patients with the diagnosis of amebic liver abscess 48, or 79%, had antibodies to the SREHP fusion protein (Table 3). Seropositivity was higher in the samples from Mexico (30/33, 91%) than from Durban (11/17, 65%) or San Diego (7/10, 70%). A patient from San Diego with two distinct episodes of amebic liver abscess was seropositive in a sample taken after the second amebic liver abscess, but seronegative in a sample taken after the first episode. The one patient from St. Louis had anti-SREHP antibodies at the time of his presentation with amebic liver abscess, but no antibodies were present 1 year later. Only 4 patients with intestinal amebiasis were examined in this study, all 4 had anti-SREHP antibodies. None of the healthy controls from St. Louis had anti-SREHP antibodies.

To compare the sensitivity and specificity of Western blotting using the SREHP fusion protein with AGD in a highly endemic area, sera from 36 patients from Durban were analyzed separately (Table 4). Of the 17 patients with amebic liver abscess and positive AGD, 11 or 65% had anti-SREHP antibodies. Nine patients with positive AGD did not have acute amebic disease. Only 1 of these patients had antibody to SREHP.

Three finding emerge from this Example. First, is the discovery that antibodies to SREHP are found among most patients with the diagnosis of amebic liver abscess. This held true for patients from two endemic areas, Mexico City and Durban, which exhibit differences in zymodeme distribution [Gathiram and Jackson, Lancet 1985; i: 719–721]. This suggests that SREHP is probably found on most, if not all, pathogenic strains of *E. histolytica*, and is consistent with the limited data from Northern blot study of axenic strains in Example 1. The inability to detect anti-SREHP antibodies in 21% of patients with liver abscess may represent failure of those individuals to make antibodies to SREHP, sensitivity problems with the assay, or different timing of the development of a serologic response to SREHP. However one cannot exclude the possibility that there may be strains of *E. histolytica* that do not possess an antigenically similar molecule.

A second finding is that a recombinant *E. histolytica* antigen can be utilized in a test for invasive amebiasis. The use of the recombinant fusion protein offers the advantages of testing with a defined antigen, rather than the crude preparations of amebic lysates used in most assays, and could facilitate the standardization of assays for amebiasis. In addition a recombinant fusion protein, produced in large quantities without the need for a source of *E. histolytica* trophozoites, may be a cost effective way of producing antigen for mass use. This is an important consideration in areas endemic for amebiasis where resources for health services are limited.

The most noteworthy finding is the correlation between the presence of antibodies to SREHP and acute invasive amebiasis. While clearly less sensitive (65%) in the Durban population of patients with amebic liver abscess (all of whom had positive AGD), detection of antibodies to SREHP was a much more specific indicator of acute amebic disease. Among the 19 ill patients who did not have acute invasive amebiasis, there was only 1 "false positive" (5%) with the SREHP test, as opposed to 9 "false positive" (47%) (probably true positives, representing previous infection with pathogenic *E. histolytica* strains) with AGD. This difference may reflect the reduced sensitivity of a single antigen test with SREHP, as opposed to the multiple antigen AGD test. A recent study measuring the serologic response to a monoclonal antibody purified *E. histolytica* antigen among patients with positive IHA serology also demonstrated a decreased sensitivity with an increased specificity for the single antigen test [Torian et al, *J. Infect. Dis.* 159, 794–97 (1989)]. A longitudinal study of patients with amebic liver abscess will be needed to determine what proportion of patients develop SREHP seropositivity, and whether SREHP seropositivity is shorter lived than that detected with the AGD, CIE, or IHA tests.

TABLE 2

| Diagnosis | Mexico City | San Diego | Durban | St. Louis | TOTAL |
|---|---|---|---|---|---|
| Amebic liver abscess | 33 | 10 | 17 | 1 | 61 |
| Amebic colitis | | 4 | | | 4 |
| Non-amebic disease | | | 19 | | 19 |
| Healthy controls | | | | 6 | 6 |
| | | | | | 90 |

TABLE 3

| | Serologic response to SREHP | |
|---|---|---|
| Diagnosis | anti-SREHP antibodies | % positive |
| Amebic liver abscess | 49/61 | 79 |
| Amebic colitis | 4/4 | 100 |
| Non-amebic disease (endemic area) | 1/19 | 5 |
| Non-endemic controls | 0/6 | 0 |

TABLE 4

| | Comparison of anti-SREHP Western blot vs. AGD in Durban samples | | | |
|---|---|---|---|---|
| Diagnosis | AGD | % positive | anti-SREHP antibodies | % positive |
| All sera | 26/36 | 72 | 12/36 | 33 |
| Amebic liver abscess | 17/17 | 100 | 11/17 | 65 |
| Non-amebic disease | 9/19 | 45 | 1/19 | 5 |

Various other examples will be apparent to the person skilled in the art after reading the present disclosure without departing from the spirit and scope of the invention. It is intended that all such other examples be included within the scope of the appended claims.

What is claimed is:

1. A serologic method for the detection of amebiasis comprising treating an aqueous dilution of a sample of the blood serum of a test host with a protein having the following amino acid sequence of a fusion protein having said amino acid sequence fused to the N-terminal two-thirds of the trpE gene of *E. coli*, assaying the resulting immunological reaction product and comprising against a control standard Met Phe Ala Phe Leu Leu Phe Ile Ala Phe Thr Ser Ala Thr Asn　15

Ile Ile Leu Asp Leu Asp Gln Glu

Val Lys Asp Thr Asn Ile Tyr　30

Gly Val Phe Leu Lys Asn Glu Ala

Ser Pro Glu Lys Leu Glu Glu　45

Ala Glu Glu Lys Glu Lys Ser Ser

Ser Ala Lys Pro Glu Ser Ser　60

Ser Asn Glu Asp Asn Glu Asp Asp

Glu Asp Glu Lys Ala Ser Ser　75

Ser Asp Asn Ser Glu Ser Ser Ser

Ser Asp Lys Pro Asp Asn Lys　90

Pro Glu Ala Ser Ser Ser Asp Lys

Pro Glu Ala Ser Ser Ser Asp　105

Lys Pro Asp Asn Lys Pro Glu Ala

Ser Ser Ser Asp Lys Pro Asp　120

-continued

Asn Lys Pro Glu Ala Ser Ser Ser
Asp Lys Pro Asp Asn Lys Pro 135
Glu Ala Ser Ser Ser Asp Lys Pro
Asp Asn Lys Pro Glu Ala Ser 150
Ser Ser Asp Lys Pro Asp Asn Lys
Pro Glu Ala Ser Ser Thr Asn 165
Lys Pro Glu Ala Ser Ser Thr Asn
Lys Pro Glu Ala Ser Ser Thr 180

-continued

Asn Lys Pro Glu Ala Ser Ser Thr
Asn Lys Pro Glu Ala Ser Ser 195
Thr Ser Asn Ser Asn Asp Lys Ser
Gly Ser Ser Ser Asp Asn Asp 210
Asn Asn Asn Leu Asp Ala Ala Ser
Ser Pro Phe Ile Val Phe Cys 225
Ala Ile Ile Ile Ala Ile Ile Phe
233.

* * * * *